United States Patent [19]

Fischer et al.

[11] Patent Number: 5,633,350

[45] Date of Patent: May 27, 1997

[54] METHOD FOR THE ISOLATION AND PURIFICATION OF VITAMIN K-DEPENDENT PROTEINS

[75] Inventors: Bernhard Fischer, Vienna; Artur Mitterer, Orth/Donau; Friedrich Dorner, Vienna, all of Austria

[73] Assignee: Immuno Aktiengesellschaft, Vienna, Austria

[21] Appl. No.: 394,508

[22] Filed: Feb. 27, 1995

[30] Foreign Application Priority Data

Feb. 28, 1994 [DE] Germany ............... 44 06 515.9

[51] Int. Cl.⁶ .................................................... A61K 35/14
[52] U.S. Cl. .................... 530/381; 530/380; 530/382; 530/384; 530/413; 530/416
[58] Field of Search .................................. 530/380, 381, 530/382, 384, 413, 416

[56] References Cited

U.S. PATENT DOCUMENTS 5,330,907  7/1994  Philapitsch et al. ............... 435/217

*Primary Examiner*—Edward J. Cain
*Attorney, Agent, or Firm*—Foley & Lardner

[57] ABSTRACT

A method for the separation of vitamin K-dependent proteins from non-vitamin K-dependent accompanying proteins is described wherein the method is characterized in that at least anion exchange chromatography and optionally affinity chromatography is carried out as well. The method is suitable especially for the purification of Factor II, VII, IX, X as well as Protein S, Protein C and Protein Z. With the aid of the method according to the invention a vitamin K-dependent protein is obtained which is present at a purity of 95%.

17 Claims, 12 Drawing Sheets

Fig.1 PURIFICATION OF rPS FROM CELL CULTURE MEDIUM BY CHROMATOGRAPHY ON Q-HYPER D.

Fig. 3A    Fig. 3B

ANALYSIS OF rPS BY SDS-POLYACRYLAMIDE GEL ELECTROPHORESIS
(A: CELL CULTURE SUPERNATANT; B: PURIFIED rPS).

Fig. 4 PURIFICATION OF rFa IX FROM CELL CULTURE MEDIUM BY CHROMATOGRAPHY ON Q-HYPER D.

Fig. 5 PURIFICATION OF rFa IX BY CHROMATOGRAPHY ON Q-HYPER D WITH ADDITION OF CALCIUM IONS.

Fig. 6A  Fig. 6B

ANALYSIS OF rFa IX BY SDS-POLYACRYLAMIDE GEL ELECTROPHORESIS
(A: CELL CULTURE SUPERNATANT; B: PURIFIED rFa IX).

Fig. 8  PURIFICATION OF rFa IX BY COUPLED CHROMATOGRAPHY ON Q-HYPER D AND HEPARIN-SEPHAROSE

Fig. 9
ANALYSIS OF PURIFIED rfa IX BY SDS-POLYACRYLAMIDE GEL ELECTROPHORESIS.

Fig. 10 PURIFICATION OF rFa II FROM CELL CULTURE MEDIUM BY CHROMATOGAPHY ON FRAKTOGEL EMD TMAE 650.

Fig. 12A  Fig. 12B

ANALYSIS OF rFa II BY SDS-POLYACRYLAMIDE GEL ELECTROPHORESIS
(A: CELL CULTURE MEDIUM; B: PURIFIED Fa II).

METHOD FOR THE ISOLATION AND PURIFICATION OF VITAMIN K-DEPENDENT PROTEINS

Aside from the naturally occurring proteins, it is possible today, with the aid of gene technology methods, to produce mammalian proteins by recombinant techniques, especially human proteins. For this purpose, host cells transformed or transfected with foreign DNA are cultured, wherein in the case of eucaryotic host cells the recombinantly produced protein is released in soluble form into the cell culture medium (R. G. Werner and W. Berthold, Arzneim.-Forsch. Drug Res. 38, 422–428 (1988)). However, since the host cells also release other proteins into the cell culture medium in addition to the desired recombinantly produced protein, it is necessary to enrich and/or isolate the desired protein in one or more purification steps. Concerning this, methods are needed which effectively and selectively permit the isolation of recombinant proteins from the cell culture medium.

As a rule, physical and chemical properties of the proteins are used for the purification of recombinant proteins. Such properties are the size of the proteins, the natural charge of the surface, their hydrophilicity or solubility. Additional purification methods concern the binding with other molecules, such as for example antibodies. The same applies for the purification of proteins from natural sources. Here as well, based on the physical and chemical properties of a protein, a separation of the same occurs from the remaining accompanying proteins.

Vitamin K-dependent proteins were purified so far according to such methods as protein precipitation, ion exchange chromatography and gel filtration M. Bertina and J. J. Veltkamp, Haemostasis and Thrombosis, (Ed. A. L. Bloom and D. P. Thomas, Churchill Livingstone, New York, 1987, 116–130). B. Dahlbäck (Biochem. J. 209, 837–846 (1983)) describes a purification method for Protein S (PS). After a barium citrate precipitation, PS is isolated on DEAE-Sephacel. J. Malm et al., (Eur. J. Biochem. 187, 737–743 (1990)) purified recombinant PS (rPS) by affinity chromatography on a monoclonal antibody. Factor IX (FaIX) was isolated by B. Osterud and R. Flengsrud (Biochem. J. 145, 469–474 (1975)) by barium sulfate precipitation and ion exchange chromatography on cellulose. Monoclonal antibodies were used by H. C. Kim et al., (Sem. Hematol. 28(3) Suppl. 6, 15–19 (1991) for the purification of FaIX.

U.S. Pat. No. 5,055,557 describes a method for the purification and concentration of vitamin K-dependent proteins from plasma as well as recombinantly produced proteins with the aid of a immunoadsorbent by using a monoclonal antibody.

In the above named methods attention must be paid to the fact that the properties of many proteins do not appreciably differ from each other which makes their fractionation more difficult. Therefore, it is necessary to apply combinations of precise, inter-coordinated purification steps in order to take advantage optimally of differences in the properties of the proteins.

A number of proteins naturally occurring in human and animal blood can bind divalent cations. Such proteins are synthesized in a vitamin K-dependent process in the cell wherein cation binding sites arise by the conversion of glutamic acid (Glu) to gamma carboxy glutamic acid (Gla). These cation binding sites can then be saturated by calcium ions ($Ca^{2+}$). Beside calcium ions, these cation binding sites are also capable, as a rule, of binding divalent strontium or barium (B. Furie and B. C. Furie, Cell 53, 505–518 (1988)).

Many of these vitamin K-dependent proteins are components of the blood plasma and play an important role in homeostasis. The gamma carboxy glutamic acid groups in these vitamin K-dependent proteins are found in the structurally homologous N-terminal Gla regions (A. Tulinsky, Thromb. Haemost. 66, 16–31 (1991). Among these calcium ion binding proteins with homologous Gla regions are, among others, Protein S (PS), Protein C, Factor IX (FaIX), Factor II, Factor VII, Factor X and Protein Z.

As a consequence of the binding of calcium ions these proteins demonstrate definitively altered properties in comparison to non-calcium binding proteins. This difference is exploited in EP 363 126 for the purification of proteins. EP 363 126 describes a method for the isolation of vitamin K-dependent proteins which are obtained recombinantly. Thereby, the divalent cations are completely removed by addition of a chelator component to the culture medium before the actual protein isolation, and the protein is thereby capable to bind to an ion exchange resin such as Mono Q. Furthermore, the protein is eluted from an anion exchanger by addition of NaCl and $Ca^{2+}$ ions. Thereby, a 58% enriched product (Protein C) was obtained. The impurities (42%) constitute such proteins which are also released from the ion exchanger at the applied salt concentration (0.15M). In a further purification step, the obtained protein-cation complex is adsorbed on a column on which immobilized EDTA is bound, washed, and the protein eluted. The proteins in the eluent are bound to an in-line ion exchanger and eluted with a salt gradient. After addition of $CaCl_2$ in the eluent, the protein-cation complex is adsorbed on a hydrophobic column and the desired protein is eluted by EDTA buffer.

The disadvantage of the method described in EP 363 126 is that a widespread conformation change of the vitamin K-dependent protein occurs through the multiple removal and addition of calcium ions which leads to changes of the properties of the protein (A. E. Johnson et al., Biol. Chem. 258, 5554–5560 (1983); J. Stenflo, J. Biol. Chem. 251, 355–363 (1976)). In contrast to this, a process is made available with the method according to the invention which does not possess these disadvantages because no process step for the removal of divalent metal ions, for example by chelators, is necessary during the entire purification process.

The advantage of the present invention is that the original conformation and stability of the vitamin K-dependent protein is preserved during the purification.

EP 354 354 describes a method for the enrichment of the blood clotting factors II, VII, IX and X. The above named prothrombin-complex factors are isolated by adsorption on an matrix carrying alpha hydroxyl amino groups, wherein especially Factor IX is strongly bound. As a function of the ion strength, the Factors II, VII and X are previously eluted. The addition of calcium ions do not play a roll in this method.

EP 317 376 describes a method for the separation of a Factor IX-containing human plasma fraction wherein cryoprecipitate is at first chromatographically prepurified, then a separation by anion exchange chromatography and selective elution through a buffer with increasing ionic strength is performed, and finally affinity chromatography on Heparin-Sepharose with selective elution is carried out. This method also does not consider the altered protein properties of Factor IX in the presence or absence of calcium ions.

The object of the present invention is to make available a method for the separation of vitamin K-dependent and calcium ion binding proteins from non-vitamin K-dependent accompanying proteins from solutions without requiring the necessity of removal of calcium ions and a possible denaturation of proteins associated with it. This method, which can be carried out with enriched protein solutions from natural sources as well as with cell culture supernatants of recombinant protein production, should be simple and lead to highly pure vitamin K-dependent proteins.

The above object is achieved by the present invention by providing methods of separating a vitamin K-dependent protein from non-vitamin K-dependent accompanying proteins, and thus can be used for isolating vitamin K-dependent and non-vitamin K-dependent proteins. The vitamin K-dependent proteins separated according to the invention include factor II, factor VII, factor IX, factor X, protein S, protein C and protein Z. The proteins can be obtained with the aid of gene technology methods, and can be isolated from the culture supernatant of transformed or transfected cells.

The separation of vitamin K-dependent proteins from non-vitamin K-dependent accompanying proteins from a protein-containing solution is characterized by adding calcium ions to the solution and then bringing the calcium-containing solution into contact with an anion exchanger under conditions in which the accompanying non-vitamin K-dependent proteins, but not the vitamin K-dependent protein, are adsorbed. The resulting solution containing the vitamin K-dependent protein can be brought into contact with an anion exchanger under conditions in which the vitamin-K dependent protein is adsorbed. The vitamin K-dependent protein can be washed, and eluted, and optionally the ionic strength of the eluent can be reduced. The calcium employed according to the method can be provided by adding $CaCl_2$ at a minimum concentration of 1.0 mM. Preferably, the protein containing solution has a pH value between 4 and 9.

Optionally, any non-adsorbed vitamin K-dependent protein is adsorbed on an affinity substrate and selectively eluted. Appropriate affinity substrates include heparin binding substrate materials, heparin-sepharose and heparin agarose. Preferably, when employing an affinity substrate, the ionic strength of the protein containing solution after elution is reduced to 0.15 to 0.2M.

The steps of the method can be carried out in any combination or order. In one embodiment, the separation step is carried out with the same anion exchanger, preferably with the aid of chromatography. The anion exchanger can have hyperdiffusion properties, and can include Q-Hyper D®. Optionally, the anion exchanger can possess a tentacle structure. The invention also comprises the highly pure vitamin K-dependent proteins isolated with the aid of these methods.

For example cell culture supernatants as well as cell culture medium processed in another way, supernatants from tissue cultures or protein solutions from natural sources which comprise vitamin K-dependent proteins are first chromatographed over an anion exchanger in the method according to the invention. A specific removal of divalent cations from the protein solution before the chromatography step is not required in contrast to the method described in EP 363 126. Rather, it was surprisingly determined that by the addition of small amounts of calcium ions at low salt concentration no binding of the vitamin K-dependent protein, yet binding of non-vitamin K-dependent proteins, occurs on the anion exchanger. For the first time, a new type of anion exchanger with hyperdiffusion properties, for example Q-Hyper D® (Sepracor) was used in the method according to the invention for the separation of vitamin K-dependent and non-vitamin K-dependent proteins. Anion exchange chromatography is followed then by affinity chromatography—as long as a further protein purification is desired.

According to the invention, the vitamin K dependent protein solution can be enriched by an additional protein concentration step without previous removal of divalent cations from the protein solution, subsequently filtered through an anion exchanger, and optionally chromatographed over an affinity column as well.

According to a preferred alternative the protein concentrate enriched in a prepurification step (1st step) is filtered through an anion exchanger (2nd step) and then directly applied on an affinity column. The preferred combination is characterized as follows:

(a) A solution comprising a vitamin K-dependent protein is brought into contact with anion exchanger wherein the vitamin K-dependent protein adsorbs on the exchanger and subsequently is eluted with increasing salt concentration; after that the salt concentration of the eluent is reduced;

(b) calcium ions are added to the eluent from (a) and this is again brought into contact with anion exchanger under conditions in which the accompanying proteins, yet not the vitamin K-dependent protein, is adsorbed;

(c) the non-adsorbed vitamin K-dependent protein from (b) is adsorbed on an affinity substrate and selectively eluted.

The above named preferred combination of method steps is more closely illustrated as follows:

For the protein concentration step (1st step) the solution which comprises a recombinant or natural vitamin K-dependent protein is brought in contact with an anion exchanger. This can occur simply by mixing or guiding over a column. Moreover, the vitamin K-dependent protein is found together with the accompanying proteins in a salt solution of lower concentration (minimal salt concentration). Under these conditions, the vitamin K-dependent protein is bound on the anion exchanger together with a number of other proteins. By increasing the salt concentration (ionic strength) vitamin K-dependent protein is thus hereinafter selectively released from the exchanger.

Cell culture supernatants comprise, as a rule, a dye which indicates the pH status. This dye, such as Phenol Red, clouds the clear protein solution, binds strongly to usual anion exchangers such as Q Sepharose Fast Flow (Pharmacia) or MacroPrep® (Bio-Rad), and adsorbs the light at the wave length of protein determination, i.e. 280 nm. This leads to an obstruction of the purification of proteins from cell culture medium. In order to make an improvement here, cell culture supernatants according to the invention were, for the first time, filtered over an anion exchanger with hyperdiffusion properties (Q-Hyper D®, Sepracor). Thereby, it was shown that the unspecific binding of the dye Phenol Red is reduced to a minimum by using Q-Hyper D as an anion exchanger. The dye is already eluted from the anion exchanger at salt concentrations under the minimal concentration. In this way the eluted proteins could be better detected during the chromatography. Moreover, a disturbing competitive reaction between the proteins and the dye on the ion exchanger is avoided to a large extent.

The further anion exchange chromatography (2nd step) consists in the fact that the ionic strength of the solution comprising the vitamin K-dependent protein is reduced to a value under the minimal salt concentration by dialysis or dilution with salt-free buffer and small amounts of calcium ions are added. Then the protein solution is again brought in contact with the anion exchanger and/or filtered through this. Thereby, it was surprisingly determined that vitamin K-dependent proteins do not bind on the anion exchanger and the non-vitamin K-dependent accompanying proteins adsorb on the substrate. This is a result of the different charge of the proteins owing to the binding of Ca ions. The vitamin K-dependent protein, now further purified from the contaminating proteins of the preliminary stage, are thereby directly obtained (without further salt dependent elution).

In many cases of protein purification, a combination of a prepurification step (1st step) with a purification on an anion exchanger (2nd step) is sufficient. Thereby, the second purification step is all the more effective, the less the vitamin K-dependent protein to be separated is contaminated with accompanying proteins.

In the second purification step on the anion exchanger, the vitamin K-dependent protein is not bound on the anion exchanger by the selection of a certain salt concentration below the minimal salt concentration of the band width and by the addition of calcium ions.

By the exploitation of the calcium binding properties of the vitamin K-dependent proteins with Gla-region, these are separated from the accompanying proteins in that, at certain ionic strengths, only the accompanying proteins are bound on the anion exchanger, however, the vitamin K-dependent proteins pass through the anion exchanger without binding to it. Therefore, aside from vitamin K-dependent proteins from natural sources, the method according to the invention is particularly suitable for the purification of recombinant vitamin K-dependent proteins with Gla-region, such as for example Protein C, Factor IX, Factor II, Factor VII, Protein S and Protein Z.

For the above named steps 1 and 2, it is preferred to used the same anion exchanger, wherein particularly good results are obtained when the anion exchange chromatography occurs on a column.

In the in-line method (3rd step), namely the affinity chromatography, a binding of the vitamin K-dependent protein on the affinity matrix occurs. In this step, the vitamin K-dependent protein is adsorbed on the affinity matrix. In this case, the prepurification step connected in series to the anion exchanger proves to be particularly advantageous because by this a number of contaminating proteins were removed. This fosters the elution of the vitamin K-dependent protein from the affinity matrix and allows the isolation of the desired protein in high purity.

The method according to the invention can include a virus inactivation step known to the person skilled in the art from the prior art which encompasses the treatment of the vitamin K-dependent protein solutions with physical-chemical or chemical methods. For this purpose, the treatment in the presence of antiviral substances, optionally combined with a radiation or heat treatment are considered. According to the present invention, the virus inactivation can occur before the separation of vitamin K-dependent proteins from non-vitamin K-dependent accompanying proteins.

The method according to the invention can consist of a combination of the purification steps 1, 2 and 3 which can be carried out in any order. Thereby, however, the method of separating vitamin K-dependent proteins from non-vitamin K-dependent accompanying proteins from a protein-containing solution is characterized by adding calcium ions to the solution and then bringing the calcium-containing solution into contact with an anion exchanger under conditions in which the accompanying non-vitamin K-dependent proteins, but not the vitamin K-dependent protein, are adsorbed, is always obligatory.

The FIGS. 1 to 12 show purification steps and/or results as follows:

FIG. 3B depicts electrophoresis with purified rPS);

FIG. 6B depicts electrophoresis with purified rFaIX);

FIGS. 12A and 12B Analysis of rFaII by SDS-PAGE gel electrophoresis (FIG. 12A depicts electrophoresis with a cell culture supernatant; FIG. 12B depicts electrophoresis with purified FaII).

The following Examples demonstrate the purification according to the invention of Protein S, Factor IX and Factor II

EXAMPLE 1 a) Purification of rPS by Anion Exchange Chromatography

In the following Example, a quaternary amino-type anion exchanger with hyperdiffusion properties (Q-Hyper D, Sepracor) was used.
Materials:
Column: Q-Hyper D, Sepracor; 2 cm×4 cm.
Buffer A: 20 mM Bis-Tris/HCl, pH 7,0.
Buffer B: 20 mM Bis-Tris/HCl, pH 7,0, 0.18M NaCl.
Buffer C: 20 mM Bis-Tris/HCl, pH 7,0, 0.4M NaCl.
Buffer D: 20 mM Bis-Tris/HCl, pH 7,0, 1 mM NaCl.

Recombinant protein (rPS) was isolated, based on usual laboratory methods, after infection of Veto cells (Monkey kidney cells) with vaccinia virus by cell culture technology. Vero/vaccinia expression systems and cell culture conditions are comprehensively described in F. G. Falkner et al, Thrombosis and Haemostasis, 68, 119–124 (1992) and N. Barrett et al., AIDS Res. Hum. Retrov., 5, 159–171 (1989); F. Dorner and N. Barrett, AIDS Vaccine Research and Clinical Trials, (Ed. S. D. Putney and D. P. Bolognesi), Marcel Dekker, Inc., New York (1990). The expression of rPS occurs in commercially available, synthetic DMEM medium. After cell culture, the culture supernatant was isolated by centrifugation and spiked with the synthetic protease inhibitor Pefabloc® SC, Pentapharm, to 0.1 mMol/l.

The column was regenerated corresponding to the instructions of the manufacturer and equilibrated with Buffer A. Subsequently, 485 ml of cell culture supernatant, which contained recombinant Protein S, were applied with a speed of 10 ml/min on the column. The material not bound to the column was removed with the same flow speed by washing with Buffer A. After that, the column was first eluted with Buffer B and subsequently with Buffer C. Subsequent elution occurred with Buffer D. The protein adsorption was followed during the chromatography in the normal manner at 280 nm. After execution of the chromatography, the protein concentration was determined by means of the Bradford method (M. M. Bradford, Anal. Biochem. 72, 248–254 (1976). The content of Protein S was determined by means of a commercial ELISA system (Asserachrome Protein S, Boehringer Mannheim) as well as by means of a clotting test (Protein S clotting test, Boehringer Mannheim).

It was found that almost all rPS was bound to the matrix. rPS was eluted from the anion exchanger in 0.4M NaCl (Buffer C).

By using the above named anion exchanger, the dye Bromophenol Red, commonly contained in cell culture medium, was already eluted from the column at a salt concentration of 0.18M which substantially fostered the subsequent isolation of rPS at 0.4M NaCl. This constitutes an advantage compared to the use of other anion exchangers.

Figure 1:
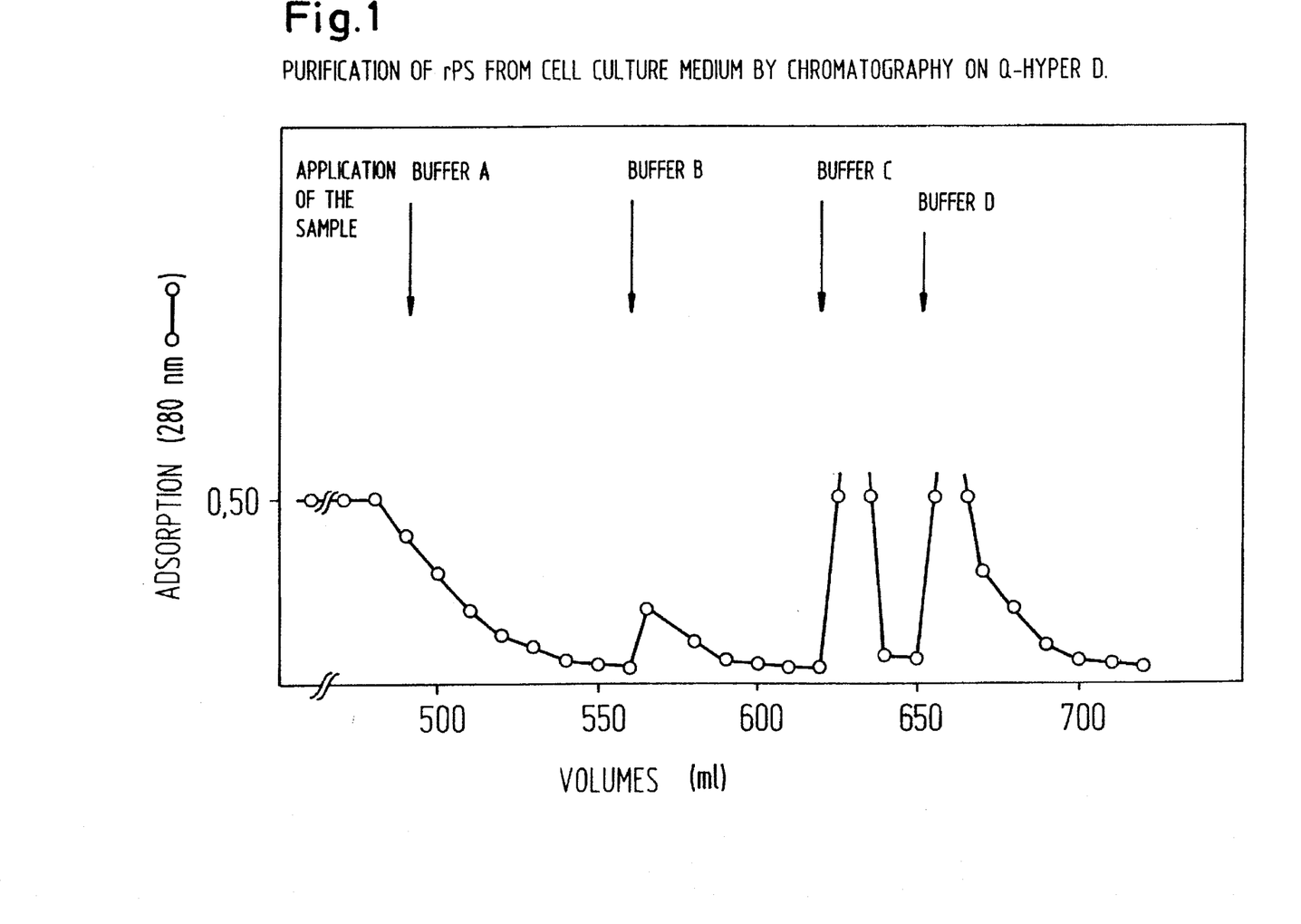
FIG. 1 Purification of recombinant Protein S from cell culture supernatant by chromatography on Q-Hyper (pre-step=1st step)

The essential results of the purification of rPS on the anion exchanger (1st step) are summarized in FIG. 1 and Table 1. By the purification described in Example 1, the amount of 3% rPS antigen to the total protein of the cell culture medium was increased to 8% rPS antigen to protein in the 0,4M NaCl fraction. The specific activity increased 25-fold.

TABLE 1

| sample | volumes (ml) | protein (mg/ml) | Protein S antigen activity (mU/ml) | | specific activity (U/mg) |
|---|---|---|---|---|---|
| cell supernatant | 485 | 0.108 | 137 | 11 | 0.1 |
| unbound fraction | 560 | 0.05 | 4 | 0 | 0 |
| 0.18M NaCl | 60 | 0.014 | 4 | 0 | 0 |
| 0.4M NaCl | 14 | 0.537 | 1700 | 1358 | 2.5 |
| 1M NaCl | 20 | 0.54 | 4 | 0 | 0 | b) Purification of rPS by Adsorption of Accompanying Proteins by Means of Anion Exchange Chromatography with Addition of Calcium Ions (2nd Step).

The same anion exchange type was used as described under 1.a).
Materials:
Column: Q-Hyper D, Sepracor; 1 cm×4 cm.
Instrument: Pharmacia FPLC LCC-500.
Buffer A: 20 mM Bis-Tris/HCl, pH 7.0.
Buffer B: 20 mM Bis-Tris/HCl, pH 7.0, 0.15M NaCl, 10 mM CaCl$_2$.
Buffer C: 20 mM Bis-Tris/HCl, pH 7.0, 1M NaCl.

The column was regenerated corresponding to the instructions of the manufacturer and equilibrated with Buffer B. Recombinant Protein S, which was isolated from cell culture supernatant as described in Example 1.a), was diluted 2.5-fold with Buffer A such that the concentration of NaCl lied under 0.18M. CaCl$_2$ with a concentration of 10 mM was added. Subsequently, the protein mixture was applied on the column and the unbound protein was washed out of the column with Buffer B. Bound protein was eluted by means of Buffer C. The course of the chromatography was followed as described in Example 1.a) and the respective protein concentration was determined.

Figure 2:
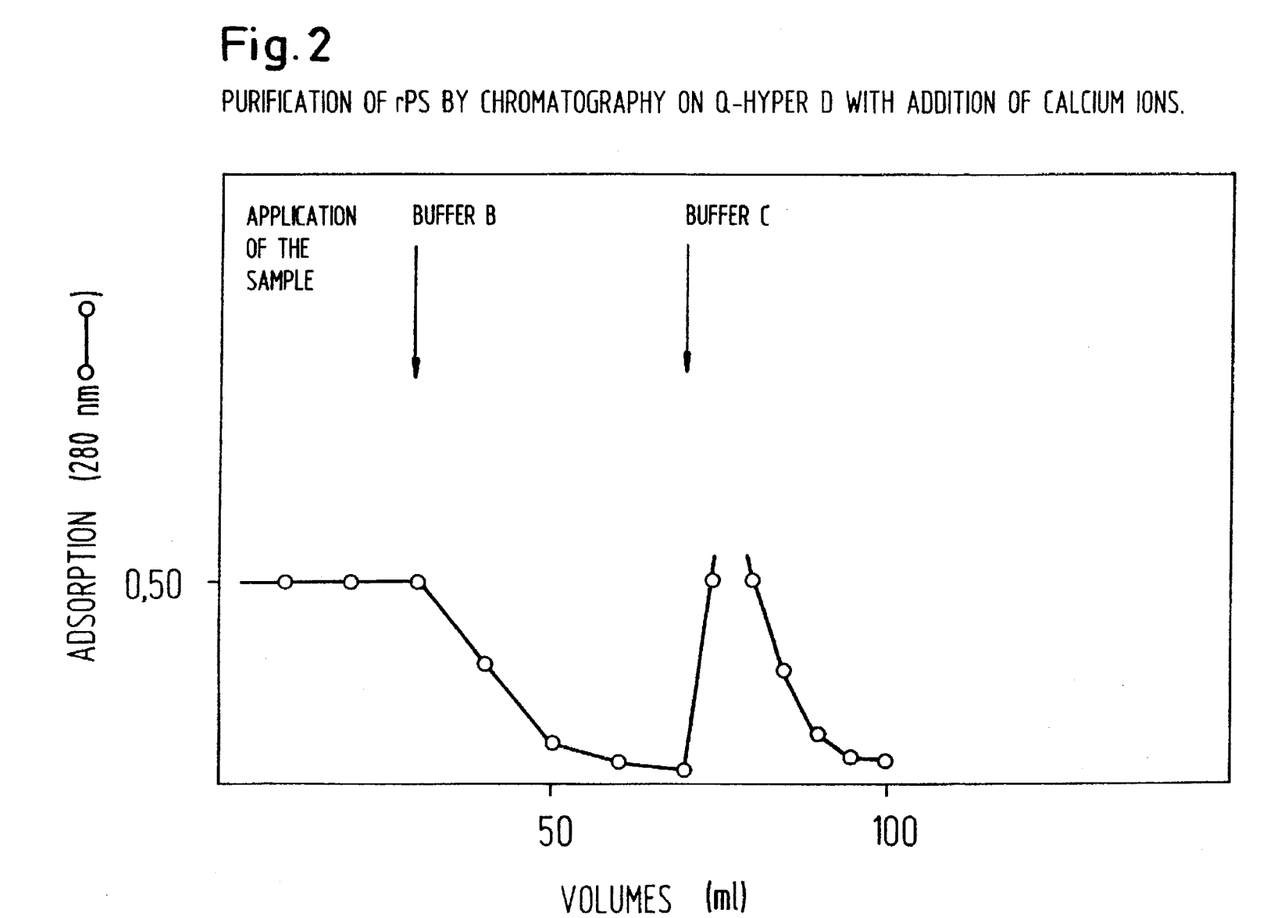
FIG. 2 Purification of recombinant Protein S by chromatography on Q-Hyper D with addition of calcium ions (=2nd step)
Figure 3A:
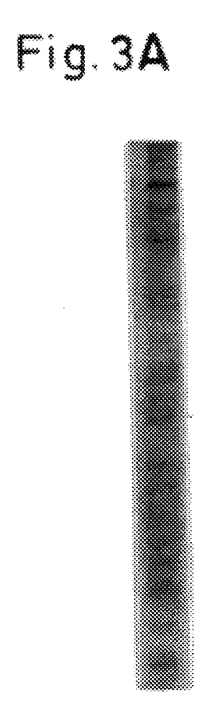
FIGS. 3A and 3B SDS-PAGE gel electrophoresis of purified recombinant Protein S (FIG. 3A depicts electrophoresis with a cell culture supernatant.
Figure 3B:
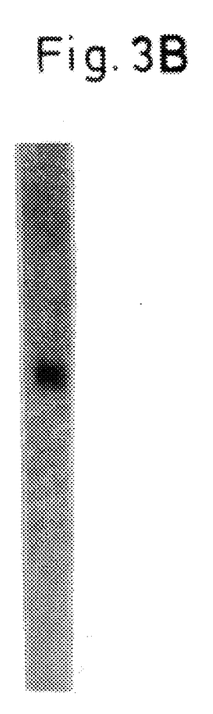

The results show that rPS passed through the column unimpeded, whereas the predominant majority of the further proteins remained stuck on the column. These contaminating proteins were then eluted with 1M NaCl. The essential results of this experiment are summarized in FIG. 2, FIGS. 3A and 3B and Table 2.

Through the purification described in Example 1.b), the antigen content of rPS was increased 12-fold in relationship to the other proteins. The specific activity increased 14-fold. The denaturing electrophoretic analysis (U.K. Laemmli, Nature 227, 680–685 (1970)) demonstrated (FIGS. 3A and 3B) that by the purification described in Example 1.b), rPS was isolated at more than 95% purity.

TABLE 2

| sample | volumes (ml) | protein (mg/ml) | Protein S antigen activity (mU/ml) | | specific activity (U/mg) |
|---|---|---|---|---|---|
| preparation from Example 1a | 34 | 0.215 | 680 | 543 | 2.5 |
| unbound fraction | 34 | 0.014 | 600 | 520 | 37 |
| 1.0M NaCl | 10 | 0.332 | 83 | 0 | 0 |

EXAMPLE 2 a) Purification of rFaIX by Anion Exchange Chromatography.

In the following Example, a quaternary amino-type anion exchanger with hyperdiffusion properties (Q-Hyper D, Sepracor) was used.
Materials:
Column: Q-Hyper D, Sepracor; 2 cm×4 cm.
Instrument: Pharmacia FPLC LCC-500.
Buffer A: 20 mM Bis-Tris/HCl, pH 5.5.
Buffer B: 20 mM Bis-Tris/HCl, pH 5.5, 0.18M NaCl.
Buffer C: 20 mM Bis-Tris/HCl, pH 5.5, 0.3M NaCl.
Buffer D: 20 mM Bis-Tris/HCl, pH 5.5, 1.0M NaCl.

Recombinant Factor IX (rFIX) was obtained in an analogous manner as for rPS (Example 1.a).

The column was regenerated corresponding to the instructions of the manufacturer and equilibrated with Buffer A. Subsequently, 1997 ml of cell culture supernatant, which contained recombinant Factor IX, were applied with a speed of 10 ml/min on the column. The material not bound to the column was removed with the same flow speed by washing with Buffer A. After that, the column was first washed with Buffer B and subsequently with Buffer C. Subsequent elution occurred with Buffer D.

The protein adsorption was followed during the chromatography in the usual manner at 280 nm. After ending the chromatography, the protein concentration was determined by means of the Bradford method (M. Bradford, Anal. Biochem. 72, 248–254 (1976). The content of Factor IX was determined by means of a commercial clotting test (Factor IX clotting, Immuno).

The results show that almost all of the rFaIX was bound to the anion exchanger. rFaIX was eluted from the anion exchanger in 0.3M NaCl. Analogous results were also obtained by using other quaternary amino anion exchangers. On the other hand, by using Q-Hyper D, the dye Bromophenol Red, normaly contained in cell culture medium, was already eluted from the column at a salt concentration under 0.3M which substantially fostered the subsequent isolation of rFaIX at 0.3M NaCl. Other anion exchangers do not have this advantageous property.

Figure 4:
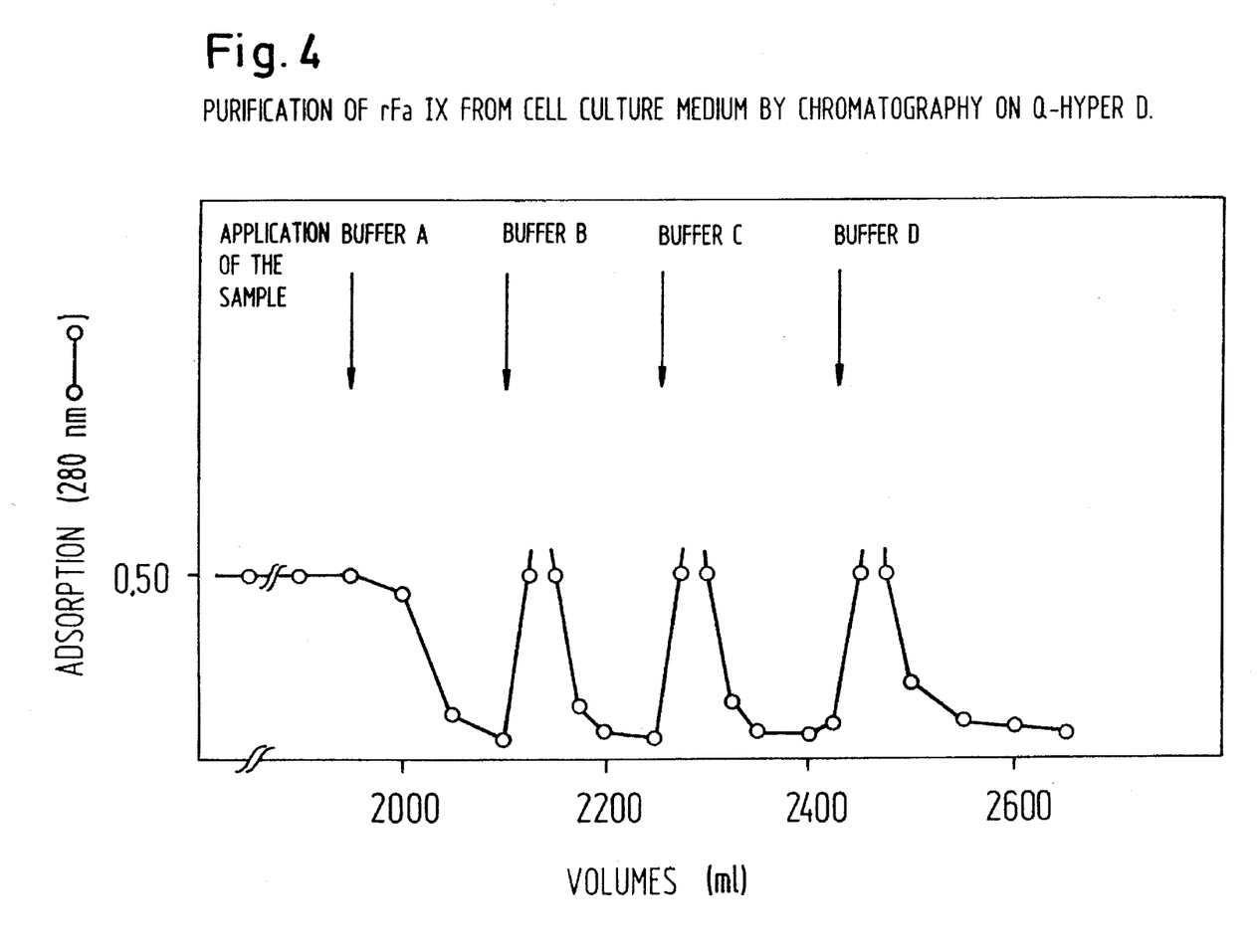
FIG. 4 Purification of rFaIX by chromatography on Q-Hyper D (1st step)

The essential results of the purification of rFaIX on the anion exchanger are summarized in FIG. 4 and Table 3. By the purification described in Example 2.a, rFaIX was enriched 20-fold; the specific activity increased by 12-fold.

TABLE 3

| sample | volumes (ml) | protein (mg/ml) | Factor IX activity (mU/ml) | specific activity (U/mg) |
|---|---|---|---|---|
| cell supernatant | 1997 | 0.178 | 100 | 0.56 |
| unbound fraction | 2100 | 0.091 | 0 | 0 |
| 0.18M NaCl | 94 | 0.382 | 162 | 0.41 |
| 0.3M NaCl | 94 | 0.300 | 2099 | 6.86 |
| 1M NaCl | 93 | 0.09 | 32 | 0.35 | b) Purification of rFaIX by Adsorption of Accompanying Proteins by Means of Anion Exchange Chromatography with Addition of Calcium Ions.

Q-Hyper D served as an anion exchanger as it was also used in Example 2.a).

Materials:

Column: Q-Hyper D, Sepracor; 2 cm×4 cm.
Instrument: Pharmacia FPLC LCC-500.
Buffer A: 20 mM Bis-Tris/HCl, pH 7.4.
Buffer B: 20 mM Bis-Tris/HCl, pH 7.4, 0.15M NaCl, 10 mM $CaCl_2$.
Buffer C: 20 mM Bis-Tris/HCl, pH 7.4, 1.0M NaCl.

The column was regenerated corresponding to the instructions of the manufacturer and equilibrated with Buffer A. 85 ml of recombinant Factor IX, as it was obtained in Example 2.a), was diluted 2-fold with Buffer A such that the concentration of NaCl was reduced to 0.15M. $CaCl_2$ was added to 10 mM. Subsequently, the protein mixture was applied and the unbound protein was washed out of the column with Buffer B. Protein bound on the column was eluted by means of Buffer C. The course of the chromatography was followed as described in Example 2.a). The protein concentrations and enzyme activities were determined.

The results show that rFaIX passed through the column unimpeded, whereas the predominant majority of the contaminanting proteins remained stuck on the column. These contaminating proteins were then eluted with 1M NaCl.

Figure 5:
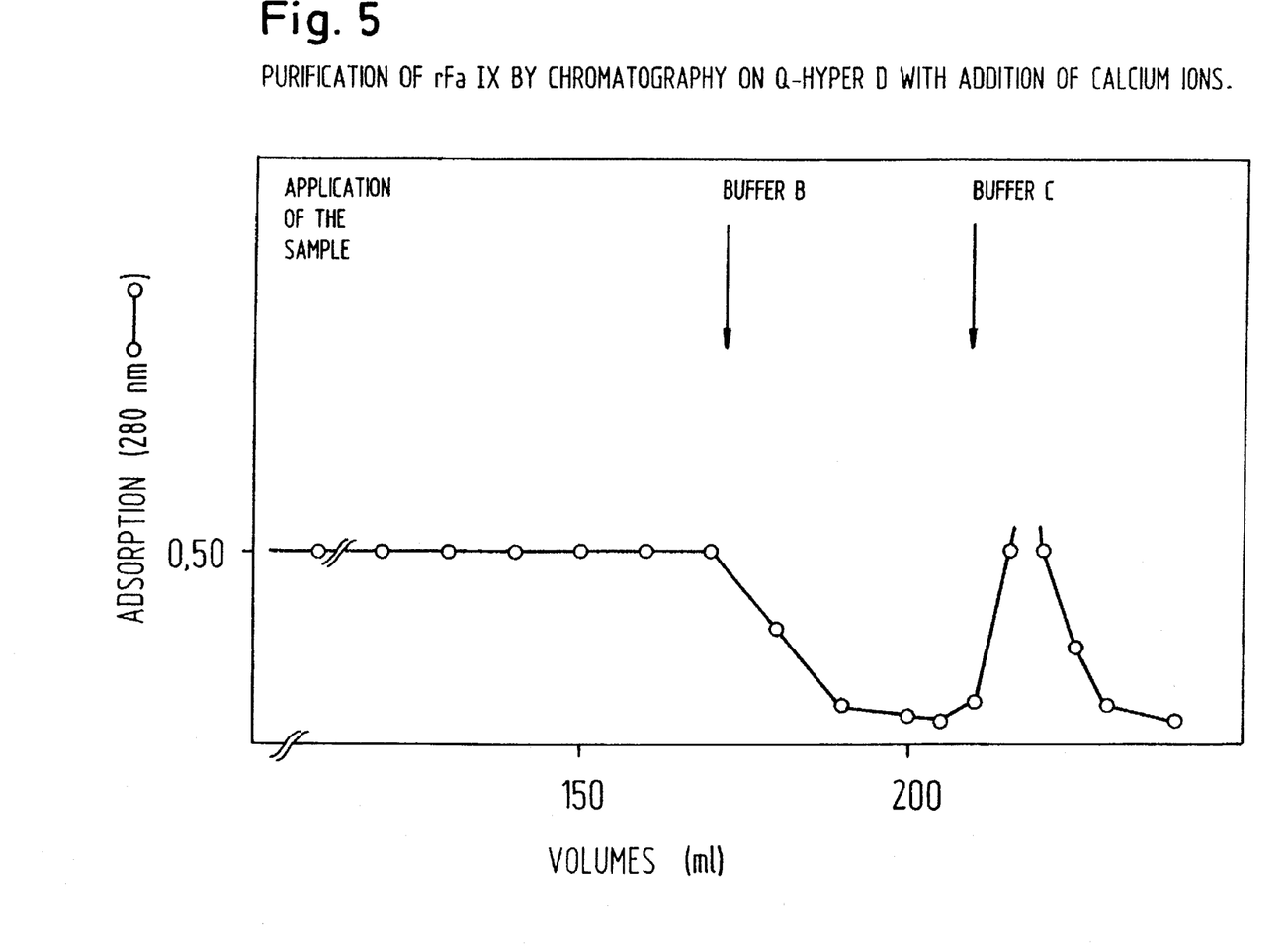
FIG. 5 Purification of rFaIX by chromatography on Q-Hyper D with addition of calcium ions (2nd step)
Figure 6A:
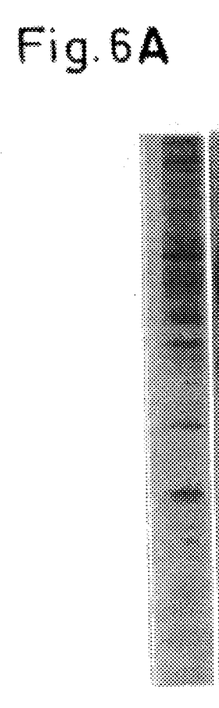
FIGS. 6A and 6B SDS-PAGE gel electrophoresis of rFaIX (FIG. 6A depicts electrophoresis with a cell culture supernatant.
Figure 6B:
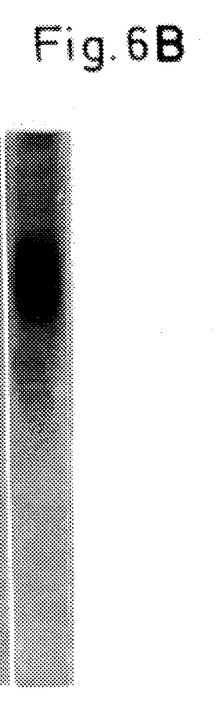

The essential results are summarized in FIG. 5, FIGS. 6A and 6B and Table 4. Through the purification described in Example 2.b), the specific activity of rFaIX increased by 4-fold. The denaturing electrophoretic analysis according to Laemmli, demonstrated (FIGS. 6A and 6B) that by the purification described in Example 2.b), rFaIX was isolated at more than 80% purity.

TABLE 4

| sample | volumes (ml) | protein (mg/ml) | Factor IX activity (mU/ml) | specific activity (U/mg) |
|---|---|---|---|---|
| preparation from Example 2a | 170 | 0.153 | 1040 | 6.7 |
| unbound fraction | 200 | 0.04 | 1076 | 27.5 |
| 1M NaCl | 20 | 0.45 | 0 | 0 | c) Purification of rFaIX by Affinity Chromatography

In the following, rFaIX, as obtained as in Example 2.a), was purified by affinity chromatography. Heparin-Sepharose was used as the affinity matrix.

Materials:

Column: HiTrap® Heparin, Pharmacia; 5 ml.
Instrument: Pharmacia FPLC LCC-500.
Buffer A: 50 mM Tris, 20 mM sodium citrate, pH 7.4.
Buffer B: 50 mM Tris, 20 mM sodium citrate, pH 7.4, 0.15M NaCl.
Buffer C: 50 mM Tris, 20 mM sodium citrate, pH 7.4, 0.3M NaCl.
Buffer D: 50 mM Tris, 20 mM sodium citrate, pH 7.4, 1M NaCl.

The column was regenerated corresponding to the instructions of the manufacturer and equilibrated with Buffer A. 78 ml of rFaIX, as it was obtained in Example 2.a), was applied on the column and the unbound protein was washed out of the column with Buffer A. Subsequently, the column was eluted with Buffer B, thereafter with Buffer C. The subsequent elution occurred with Buffer D. The course of the chromatography was followed as described in Example 2.a); the protein concentrations and enzyme activities were determined.

The results show that rFaIX was completely bound on the column, and first eluted from this by 0.3M NaCl. In this method however, further proteins were also simultaneously eluted with rFaIX and therewith not separated from rFaIX. The specific activity or rFaIX was only increased by 4.5-fold through method represented in Example 2.c).

Figure 7:
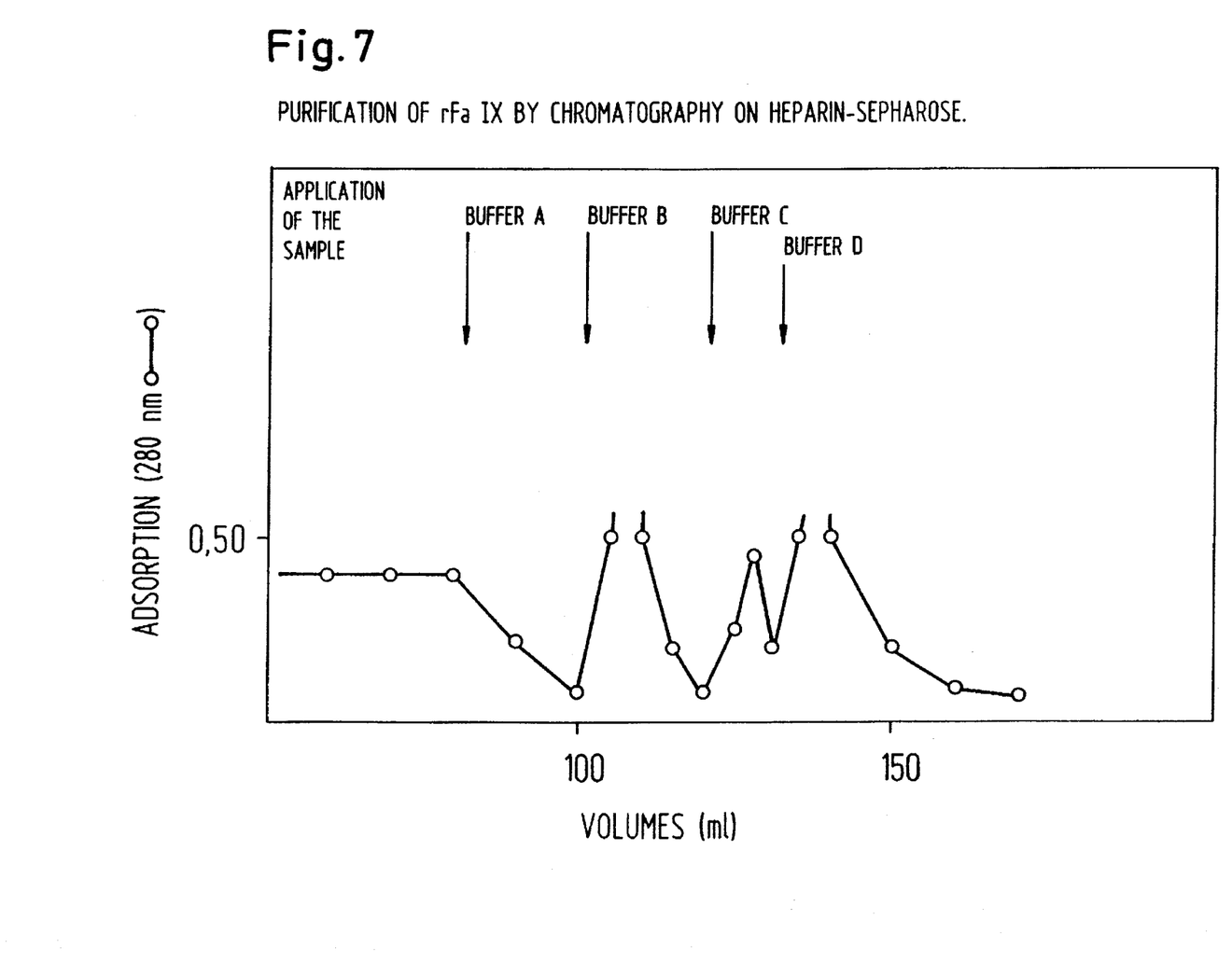
FIG. 7 Purification of rFaIX by chromatography on Heparin-Sepharose (3rd step)

The essential results are summarized in FIG. 7 and Table 5.

TABLE 5

| sample | volumes (ml) | protein (mg/ml) | Factor IX activity (mU/ml) | specific activity (U/mg) |
|---|---|---|---|---|
| preparation from Example 2a | 78 | 0.121 | 788 | 6.5 |
| unbound fraction | 90 | 0.038 | 0 | 0 |
| 0.15M NaCl | 10 | 0.10 | 0 | 0 |
| 0.3M NaCl | 22 | 0.053 | 1572 | 29.6 |

EXAMPLE 3

Purification of rFaIX by Direct Coupling of Anion Exchange Chromatography and Affinity Chromatography.

In the following Example, rFaIX, as obtained in Example 2.a), was purified in such a way that it was first applied on an anion exchanger and thereafter on an affinity chromatography column. Q-Hyper D served as the anion exchanger; this is an anion exchanger of the amino type with hyperdiffusion properties. Heparin-Sepharose (HiTrap® Heparin, Pharmacia) was used as the affinity matrix. The Q-Hyper D column was attached in direct series before the Heparin-Sepharose column. Only a flexible tube connection restricted to the minimum, optionally with a valve, was mounted between the columns.

Materials:

Column 1: Q-Hyper D®, Sepracor; 2 cm×4 cm.
Column 2: HiTrap® Heparin, Pharmacia; 5 ml.
Instrument: Pharmacia FPLC LCC-500.
Buffer A: 20 mM Tris/HCl, pH 7.4.
Buffer B: 20 mM Tris/HCl, pH 7.4, 150 mM NaCl, 10 mM $CaCl_2$.
Buffer C: 20 mM Tris/HCl, pH 7.4, 1.0M NaCl.
Buffer D: 50 mM Tris, 20 mM sodium citrate, pH 7.4, 0.15M NaCl.
Buffer E: 50 mM Tris, 20 mM sodium citrate, pH 7.4, 0.3M NaCl.
Buffer F: 50 mM Tris, 20 mM sodium citrate, pH 7.4, 1M NaCl.

The outlet of the column with the anion exchanger was directly connected with the inlet of the affinity chromatography column by a flexible tube connection such that the stream of liquid first ran through the column 1 and subsequently directly through column 2.

The columns were regenerated corresponding to the instructions of the manufacturer and equilibrated with Buffer B. 70 ml rFaIX, which was isolated from cell culture supernatant as described in Example 2.a), was diluted to 2-fold with Buffer A such that the concentration of NaCl was reduced to 0.15M. $CaCl_2$ was added until a concentration of 10 mM. Subsequently, the protein mixture was applied through the column 1 (Q-Hyper D®) at 2.5 ml/min and directly transferred on column 2 (Heparin-Sepharose), wherein unbound protein was washed from the columns with Buffer B. Thereafter, column 1 was disconnected from the affinity coulmn and the stream of liquid was directly applied on column 2. In analogy to the method represented in Example 2.c), unbound protein from the heparin column was removed by washing with Buffer D. The elution of the heparin column ensued with Buffer E. The subsequent elution was carried out with Buffer F. Analogous results were obtained when, after the application of the sample, the Q-Hyper D® column was not removed from the heparin column but instead the liquid stream for the elution of the heparin column was lead directly on the heparin column through an interconnected valve.

The proteins bound on the column 1 (Q-Hyper D®) were eluted by Buffer C.

The course of the chromatography was followed as described in Example 2.a); the protein concentrations and enzyme activities were determined.

The results show that by the application of the sample through the introduced Q-Hyper D® column, the rFaIX passes through this unimpeded and is completely absorbed on the heparin column placed thereafter. rFaIX was eluted from the latter by 0.3M NaCl.

Figure 8:
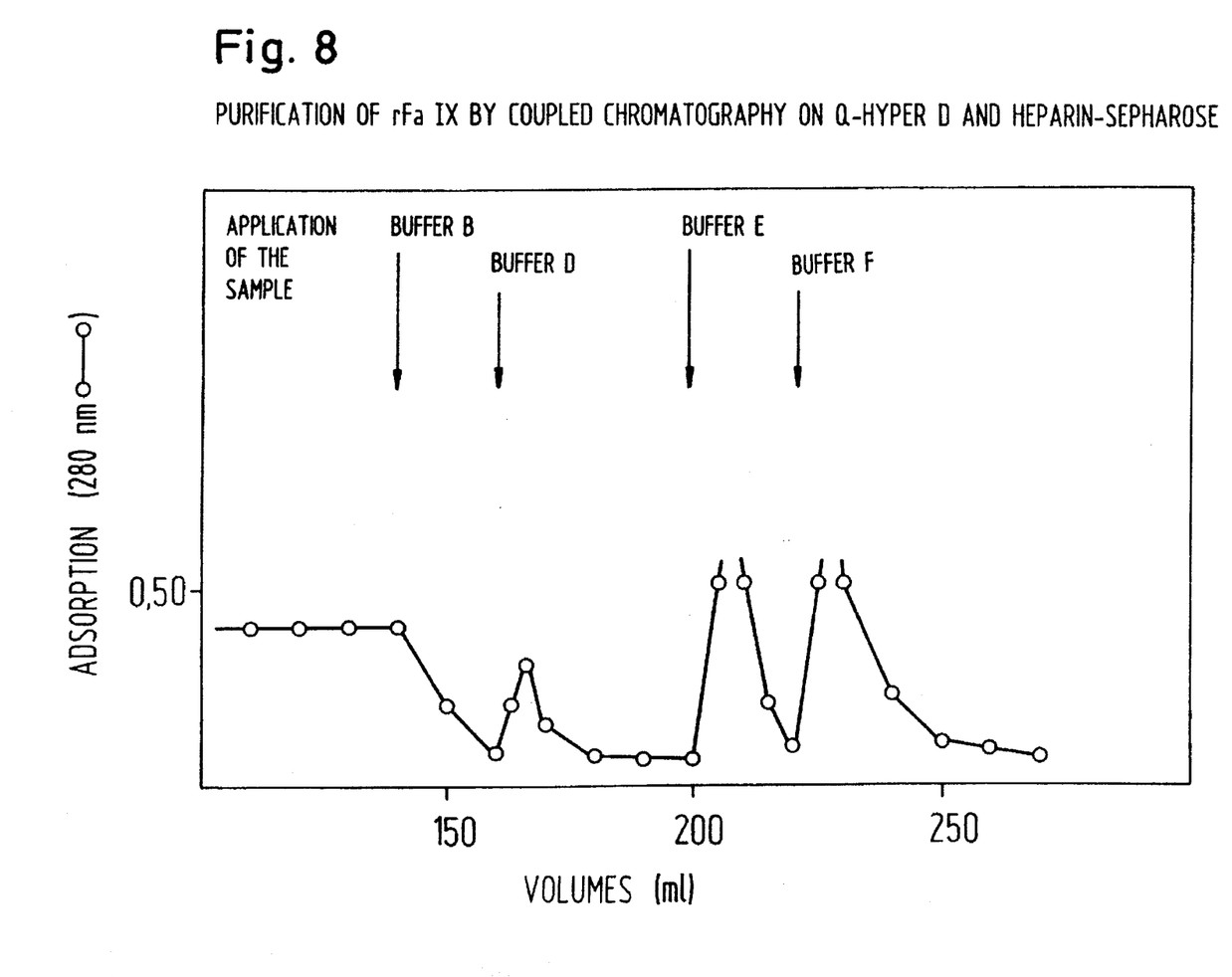
FIG. 8 Purification of rFaIX by coupled chromatography on Q-Hyper D and Heparin-Sepharose (2nd and 3rd step)
Figure 9:
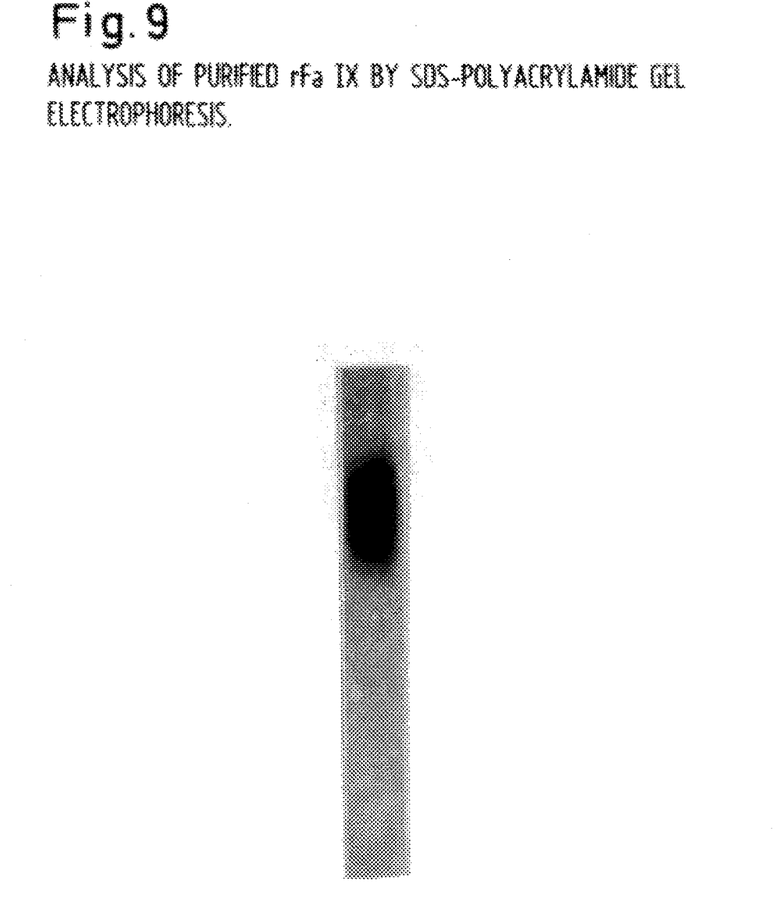
FIG. 9 SDS-PAGE gel electrophoresis of rFaIX as obtained in FIG. 8)

The essential results are summarized in FIG. 8, FIG. 9 and Table 6.

rFaIX is enriched 8.4-fold by the purification described in Example 3; the specific activity is increased by 8.8-fold. The denaturing electrophoretic analysis (according to Laemmli) showed (FIG. 9) that rFaIX is isolated at more than 95% purity by the purification described in Example 3.

In Example 3, the purification of rFaIX was carried out by a direct combination of the methods from Examples 2.a),b) and c) wherein the same starting material was employed. In comparison to the purification from Example 2.c) however, a higher enrichment and a higher specific activity were obtained through a combination of anion exchange chromatography and affinity chromatography. Through the combination of both chromatography methods, such contaminating proteins which unfavorably influence the separation process on the affinity substrate are obviously separated before hand, whereby a higher specificity and selectivity of the affinity substrate results.

TABLE 6

| sample | volumes (ml) | protein (mg/ml) | Factor IX activity (mU/ml) | specific activity (U/mg) |
|---|---|---|---|---|
| preparation from Example 2a | 148 | 0.0196 | 123 | 6.3 |
| unbound fraction | 160 | 0.01 | 0 | 0 |
| 0.15M NaCl | 32 | 0.01 | 0 | 0 |
| 0.3M NaCl | 10 | 0.019 | 1041 | 54.8 |
| 1M NaCl | 30 | 0.015 | 0 | 0 |

EXAMPLE 4

Purification of rFaII by Anion Exchange Chromatography

In the following Example, a quaternary amino-type anion exchanger with tentacle structure (Fraktogel EMD TMAE 650 M, Merck) was used.

Materials:
Column: Fraktogel EMD TMAE 650 M, Merck, 1.6 cm×5 cm.
Instrument: Pharmacia FPLC LCC-500 system.
Buffer A: 50 mM Tris/HCl, pH 7.4.
Buffer B: 50 mM Tris/HCl, pH 7.4, 200 mM NaCl.
Buffer C: 50 mM Tris/HCl, pH 7.4, 300 mM NaCl.
Buffer D: 50 mM Tris/HCl, pH 7.4, 1M NaCl.

Recombinant Factor II was isolated based on the usual laboratory methods of cell culture technology (Falkner et al, Thrombosis and Haemostasis, 68, 119–124 (1992)).

The expression of rFaII ensued in commercially obtainable synthetic DMEM medium. Cell-free culture supernatant was obtained by centrifugation.

The column was regenerated corresponding to the instruction of the manufacturer and equilibrated with Buffer A. Subsequently, 200 ml of cell culture supernatant, which contained recombinant Factor II, were applied on the column with a speed of 4 ml/min. Material not bound to the column was removed by washing with Buffer A at the same flow rate. Hereinafter, the column was first washed with Buffer B and subsequently with Buffer C. Then, subsequent elution was with Buffer D. Protein adsorption was followed in the usual way at 280 nm during the chromatography. After the chromatography, the protein concentration was determined by means of the Bradford method. The content of Factor II was determined with the aid of a clotting test (Thrombinzeit, Immuno AG).

It was found that almost the entire rFaII was bound on the anion exchange gel. rFaII was eluted from the anion exchanger by 0.3M NaCl. In addition—in contrast to other amino-type anion exchangers, as for example MacroPrep® (Bio-Rad) or Q-Sepharose Fast Flow (Pharmacia)—the dye, Bromophenol Red, commonly contained in the cell culture supernatant, was already eluted from the column at a salt concentration of 0.2M NaCl, which substantially fostered the subsequent isolation of rFaII at 0.3M NaCl.

Figure 10:
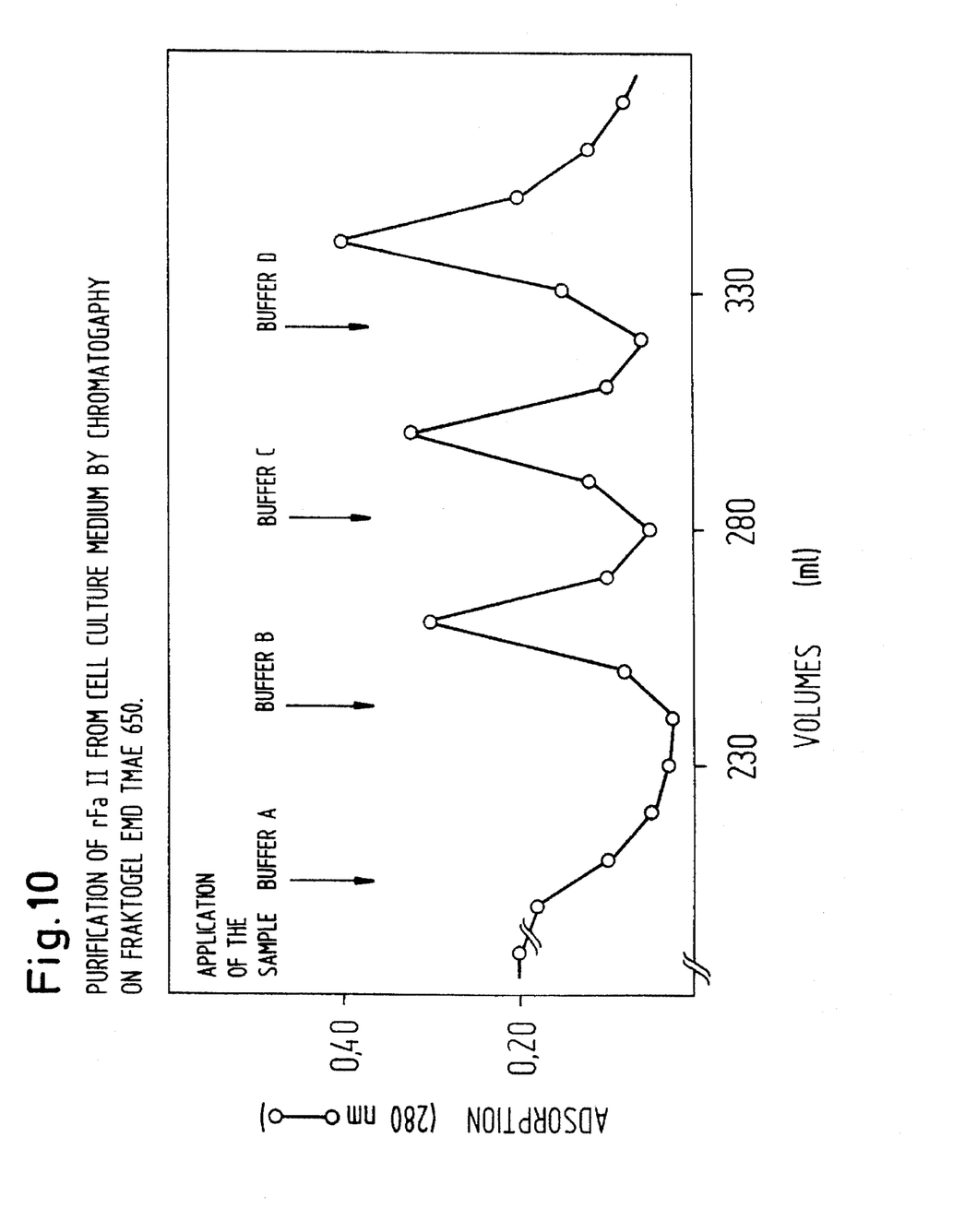
FIG. 10 Purification of rFaII from cell culture supernatant by chromatography on Fraktogel® EMD TMAE 650 (1st step)

The essential results of the purification of rFaII on the anion exchanger are summarized in FIG. 10 and Table 7. By the purification described in Example 4, the specific activity of rFaII increased by 3.5-fold.

TABLE 7

| sample | volumes (ml) | protein (mg/ml) | Factor II activity (mU/ml) | specific activity (U/mg) |
|---|---|---|---|---|
| cell medium | 200 | 0.45 | 50 | 0.1 |
| unbound fraction | 200 | 0.177 | 2 | 0.01 |
| 0.2M NaCl | 40 | 0.4 | 6 | 0.015 |
| 0.3M NaCl | 45 | 0.36 | 150 | 0.42 |
| 0.5M NaCl | 32 | 0.25 | 0 | 0 | b) Purification of rFaII by Adsorption of Accompanying Proteins by Means of Anion Exchange Chromatography with Addition of Calcium Ions.

Fraktogel EMD TMAE 650 M (Merck) served as an anion exchange resin.

Materials:
Column: Fraktogel EMD TMAE 650M, 1.6 cm×5 cm.
Instrument: Pharmacia FPLC LCC-500.
Buffer A: 50 mM Tris/HCl, pH 7.4.
Buffer B: 50 mM Tris/HCl, pH 7.4, 150 mM NaCl, 10 mM $CaCl_2$.

Buffer C: 50 mM Tris/HCl, pH 7.4, 1.0 mM NaCl.

The column was regenerated corresponding to the instructions of the manufacturer and equilibrated with Buffer B. Recombinant Factor II, as it was isolated from cell culture supernatant as described in Example 4a), was diluted 2-fold with Buffer A such that the concentration of NaCl totaled less than 0.2M. $CaCl_2$ was added until a concentration of 10 mM. Subsequently, the protein mixture was applied on the column and the unbound protein was washed out of the column with Buffer B. Bound protein was eluted by means of Buffer C.

The course of the chromatography was followed as in the preceding example and the protein concentrations were determined. The results show that rFaII passed through the column unimpeded, whereas the predominant majority of the contaminating proteins remained stuck on the column. These proteins were then eluted with 1M NaCl.

Figure 11:
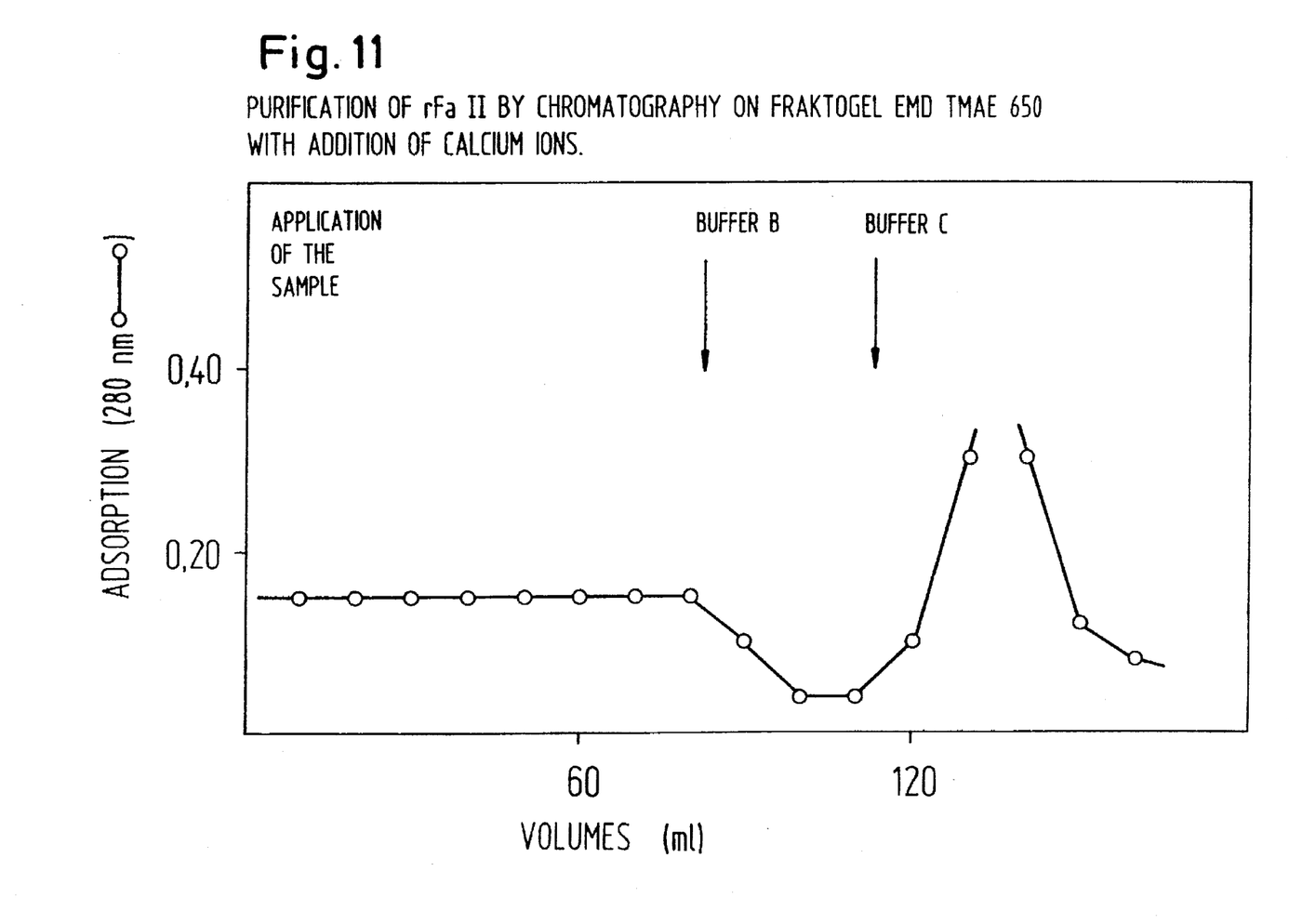
FIG. 11 Purification of rFaII by chromatography on Fraktogel® EMD TMAE 650 (2nd step)
Figure 12A:
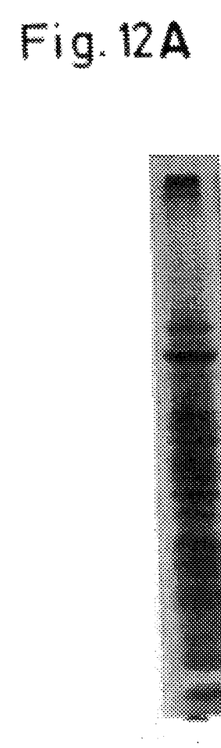
Figure 12B:
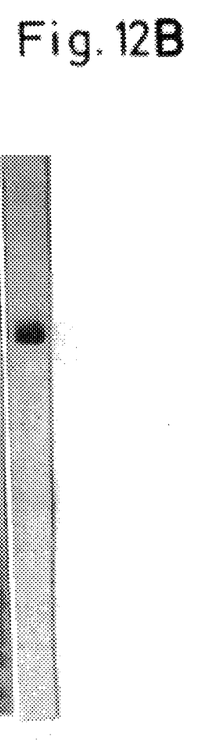

The essential results are summarized in FIG. 11, FIGS. 12A and 12B and Table 8. Through the purification described in Example 4.a) and b), the specific activity of rFaII was increased by 11-fold.

The denaturing electrophoretic analysis according to Laemmli, demonstrated (FIG. 9) that by the purification described in Example 4a and b, rFaII was isolated at more than 95% purity.

TABLE 8

| sample | volumes (ml) | protein (mg/ml) | Factor II activity (mU/ml) | specific activity (U/mg) |
|---|---|---|---|---|
| preparation from Example 4a | 80 | 0.18 | 75 | 0.41 |
| unbound fraction | 80 | 0.015 | 75 | 4.6 |
| 1.0M NaCl | 15 | 0.62 | 0 | 0 |

We claim:

1. Method for the separation of a vitamin K-dependent protein from non-vitamin K-dependent accompanying proteins from a protein-containing solution, characterized in that calcium ions are added to this solution and the calcium-containing solution is brought in contact with an anion exchanger under conditions in which the accompanying proteins, but not the vitamin K-dependent protein, are adsorbed.

2. Method according to claim 1, characterized in that the vitamin K-dependent protein-containing solution is additionally brought in contact with an anion exchanger under conditions in which the vitamin K-dependent protein is adsorbed on the exchanger, washed, eluted, and optionally, the ionic strength of the eluent is reduced.

3. Method according to claim 1, characterized in that the non-adsorbed vitamin K-dependent protein is adsorbed on an affinity substrate and selectively eluted.

4. A method according to claim 1, wherein said separation step is carried out with the same anion exchanger with the aid of chromatography.

5. Method according to claim 1, characterized in that the anion exchanger possesses hyperdiffusion properties.

6. Method according to claim 1, characterized in that the anion exchanger possesses tentacle structure.

7. Method according to claim 3, characterized in that the affinity substrate is selected from the group of the heparin binding substrate materials, Heparin-Sepharose and heparin agarose.

8. Method according to claim 7, characterized in that the ionic strength of the protein solution after the elution is decreased to 0.15 to 0.2M.

9. Method according to claim 1, characterized in that $CaCl_2$ is added until a minimum concentration of 1.0 mM.

10. Method according to claim 1, characterized in that the protein solution has a pH value between 4 and 9.

11. Method according to claim 1, characterized in that the vitamin K-dependent protein is selected from FII, FVII, FIX, FX, Protein S, Protein C and Protein Z.

12. Method according to claim 11, characterized in that the proteins are produced with the aid of gene technology methods and are isolated from the culture supernatant of transformed or transfected cells.

13. A method according to claim 1, wherein said separation allows the isolation of vitamin-K dependent proteins.

14. A method according to claim 1, wherein said separation allows the isolation of non-vitamin-K dependent proteins.

15. Highly purified vitamin K-dependent protein having a purity of at least 95%, wherein said highly purified vitamin K-dependent protein is obtainable by the steps of (A) adding calcium ions to a solution containing a vitamin K-dependent protein and non-vitamin K-dependent proteins, and (B) contacting the solution resulting from step (A) with an anion exchanger under conditions wherein only the non-vitamin K-dependent proteins are adsorbed to the anion exchanger, thereby maintaining original conformation and stability of said vitamin K-dependent protein.

16. Method according to claim 2 characterized in that the non-adsorbed vitamin K-dependent protein is adsorbed on an affinity substrate and selectively eluted.

17. A method for separating vitamin K-dependent proteins from non-vitamin K-dependent proteins, comprising the steps of:

(a) adding calcium to a solution containing the vitamin K-dependent proteins and the non-vitamin K-dependent proteins;

(b) contacting the solution of step (a) with an anion exchanger to selectively adsorb the non-vitamin K-dependent proteins, thereby separating the non-vitamin K-dependent proteins from the vitamin K-dependent proteins.

* * * * *